United States Patent [19]

Chang et al.

[11] Patent Number: 5,051,530
[45] Date of Patent: Sep. 24, 1991

[54] ESTER DERIVATIVES AND PROCESS FOR PRODUCTION THEREOF

[75] Inventors: MoonHo Chang; Han-Young Kang; HunYeong Koh; YongSeo Cho; SangChul Shim, all of Seoul, Rep. of Korea

[73] Assignee: Korea Institute of Science and Technology, Seoul, Rep. of Korea

[21] Appl. No.: 465,765

[22] Filed: Jan. 16, 1990

[30] Foreign Application Priority Data

Oct. 16, 1989 [KR] Rep. of Korea ............... 14873/1989

[51] Int. Cl.⁵ ............................................. C07C 69/66
[52] U.S. Cl. ..................................... 560/184; 560/185
[58] Field of Search ................................ 560/184, 185

[56] References Cited

PUBLICATIONS

CA109(4)24237D 1987.
CA108(4)29340V 1987.
CA106(8)58972S 1986.
CA94(11)84437S 1980.
CA83(11)96058N 1975.

*Primary Examiner*—Paul J. Killos

[57] ABSTRACT

There are provided novel ester derivatives represented by the following formula(I):

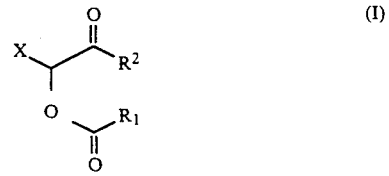

wherein, $R_1$ represents methyl, ethyl, isopropyl, t-butyl, or phenyl; $R_2$ represents phenyl, methoxy, ethoxy, isopropanoxy, or t-butanoxy; and X represents Br, and a process for preparing the same which comprises reacting an aldehyde of the formula (III) with an acid halide of the formula (IV) at 20°–80° C. in the presence or absence of solvents.

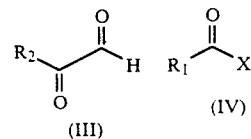

Wherein, $R_1$, $R_2$ and X have the same meaning as defined above.

10 Claims, No Drawings

ESTER DERIVATIVES AND PROCESS FOR PRODUCTION THEREOF

The present invention relates to novel ester derivatives and a process for production thereof. According to the present invention, there are provided novel ester derivatives represented by the following general formula(I). These ester derivatives are useful as modifiers for prodrug preparation in medicine.

The variable groups of the general formula(I) are explained in the following:

$$X \underset{\underset{O}{\overset{\|}{C}}-R_1}{\overset{\overset{O}{\|}}{\underset{|}{C}}-R_2} \quad (I)$$

$R_1$ represents alkyl or aryl groups. The representative alkyl groups are methyl, ethyl, n-propyl, isopropyl, n-butyl, t-butyl, and three to seven membered cycloalkyl. The aryl groups include phenyl, halophenyl, nitrophenyl, and lower alkoxy groups.

$R_2$ represents alkyl, alkoxy and aryl groups. $R_2$ as aryl represents phenyl or substituted phenyl such as halophenyl, nitrophenyl, and lower alkoxy phenyl. $R_2$ as alkoxy includes methoxy, ethoxy, isopropanoxy, t-butanoxy, and the like. $R_2$ as alkyl represents methyl, ethyl, n-propyl, isopropyl, n-butyl, t-butyl, three to seven membered cycloalkyl, and the like. X is a halogen atom (such as chlorine, bromine and iodine), toluenesulfonyloxy or methansulfonyloxy.

The ester compounds of general formula(I) react with carboxylic acids, thiocarboxylic acids or phenols to provide the corresponding carboxylic esters, thiocarboxylic esters, or phenyl ethers with the liberation of X.

Some compounds related to compound(I) are known from Can. J. Chem. 40, 1611 (1962) represented in the following formula(II).

$$X \underset{\underset{O}{\overset{\|}{C}}-R_3}{\overset{R_4}{\underset{|}{C}}} \quad (II)$$

In the formula(II) $R_3$ represents the same groups as $R_1$ explained in general formula(I), $R_4$ is methyl or ethyl group. X represents halogens such as bromine or iodine.

The present invention also provides a process for synthesizing the esters of (I) by reacting an aldehyde of (III) and an acid halide (or related compounds) of (IV).

$$R_2 \overset{O}{\underset{\|}{C}} \overset{O}{\underset{\|}{C}} H \quad R_1 \overset{O}{\underset{\|}{C}} X$$
$$(III) \qquad (IV)$$

$R_2$ in general formula (III), $R_1$ and X in general formula (IV) are the same as $R_2$, $R_1$, and X in general formula(I).

The process of the present invention is performed by reacting an aldehyde of (III) and acid halide (or related) of (IV) at 20°–80° C. with or without solvent. The amount of (IV) used in this process are usually 1–20 times (in mole ratio) with respect to the amount of (III) used.

Although this process can be done in the absence of solvent, solvent such as dichloromethane, chloroform carbon tetrachloride, tetrahydrofuran, diethyl ether, ethyl acetate, n-hexane, and pentane can be employed in this process.

Excess amount of (IV) or solvent used was removed by concentration after the reaction was completed.

The ester derivatives of general formula (I) according to the present invention can be used, for example, as protective group-introducing reagents, or as modifiers for pharmaceuticals. An ester obtained by reacting the ester of general formula (I) of the present invention with a carboxylic acid is appropriate for converting a pharmaceutical having low bioavailability into a prodrug having enhanced bioavailability.

The following Examples illustrate the present invention in more specifically.

EXAMPLE 1

Methyl bromoacetoxyacetate

In methyl glyoxylate (2.0g, 22.7mmol) was dissolved acetyl bromide (5mL, 68mmol). The reaction mixture was heated at 60°–70° C. for 90min with stirring. The mixture turned dark yellow oil by the end of the reaction. After cooling to room temperature, excess acetyl bromide was removed by concentration. Distillation of the reaction mixture under reduced pressure provided 3.6g of the product as a colorless oil (75%, 60°–75° C./1 torr)

$^1$H NMR(CDCl$_3$, δ): 6.15(1H,s), 3.96(3H,s), 2.31(3H,s)

EXAMPLE 2

Ethyl bromoacetoxyacetate

In ethyl glyoxylate (950mg, 9.3mmol) was dissolved acetyl bromide (3mL, 41mmol). The reaction mixture was heated at 60°–70° C. for 90min with stirring. The reaction mixture turned dark yellow oil by the end of the reaction. After cooling to room temperature, excess acetyl bromide was removed by concentration. Distillation of the reaction mixture under reduced pressure furnished 1.55g of the product as a colorless oil (73%, 70°–80° C./1 torr).

$^1$H NMR(CDCl$_3$, δ): 6.80(1H,s), 4.31 (2H, q,J=7Hz), 2.23 (3H,s), 1.33(3H, t,J=7Hz)

EXAMPLE 3

Isopropyl bromoacetoxyacetate

In isopropylglyoxylate (1.0g, 8.70mmol) was dissolved acethyl bromide (3mL, 41mmole). The reaction mixture was heated at 65°–75° C. for 90min with stirring. The reaction truned dark yellow oil by the end of the reaction. After cooling to room temperature, excess acetyl bromide was removed by concentration. Distillation of the reaction mixture under reduced pressure provided 1.41g of the product as a colorless oil (68%, 81°–85° C./0.8 torr)

$^1$H NMR(CDCl$_3$, δ) : 6.73(1H,s), 5.17(1H,sept,J=7Hz), 2.23(3H, s), 1.36 (6H,d,J=7Hz)

EXAMPLE 4

Isopropyl 1-bromo-1-(trimethyl acetoxy) acetate

In isopropylglyoxalate (1.0g, 7.70mmole) was dissolved pivaloyl bromide 3mL, (32mmole). The reaction mixture was heated at 75°-80° C. for 2hr with stirring. After cooling to room temperature, excess pivaloyl bromide was removed by concentration. Distillation of the reaction mixture under reduced pressure provided 1.44g of the product as a colorless oil (54% 75°-85+ C./0.4 torr).

$^1$H NMR (CDCl$_3$, δ) 6.67 (1H,s), 5.10 (1H, sept. J=7Hz) 1.33 (6H,d,J=7Hz), 1.29(9H,s)

EXAMPLE 5

Ethyl 1-bromo-1-trichloroacetoxy acetate

In ethylglyoxalate (3.20g, 31 mmole)was dissolved trichloracetyl bromide (12.0g, 51 mmole) The reaction mixture was heated at 75°-80° C. for 2hr with stirring. After cooling to room temperature, excess trichloroacetyl bromide was removed by concentration. Distillation of the reaction mixture under reduced pressure provided 4.22g of the product as a colorless oil(41%, 80°-90° C./1 torr).

$^1$H NMR(CDCl$_3$, δ) 6.76(1H,s), 4.39(2H,q,J=7Hz)1.33(3H,t,J=7Hz)

EXAMPLE 6

Isopropyl 1-bromo-1-(cyclohexanecarboxy)acetate

In isopropylglyoxalate [1.50g, 13.0mmole) was dissolved cyclohexanecarboxyl bromide {2.5g, 20mmole). The reaction mixture was heated at 75°-80° C. for 90min with stirring. After cooling to room temperature, excess trichloroacetyl bromide was removed by concentration. Distillation of the reaction mixture under reduced pressure provided 2.44g of the product as a colorless oil (60%, 90°-100° C./1 torr).

$^1$H NMR(CDCl$_3$, δ) 6.69(1H,s), 5.16(1H,sept.J=7Hz), 3.10-11.00 (17H,m)

EXAMPLE 7

Acetoxybromomethyl phenyl ketone

To phenylglyoxal monohydrate (200mg, 1.31mmole) was added acetyl bromide (1mL, 14mmole). The reaction mixture was heated at 65°-70° C. for 2hr with stirring. After cooling to room temperature, excess acetyl bromide was removed by concentration. Distillation of the reaction mixture under reduced pressure provided 283mg of the desired product as a colorless oil (79%, 100°-110° C./0.6 torr).

$^1$H NMR(CDCl$_3$, δ)8.10-7.10(6H,m), 2.16(3H,s)

EXAMPLE 8

Pivaloyloxybromomethyl phenyl ketone

To phenylglyoxal monohydrate {300mg, 1.97mmole) was added pivaloyl bromide (1mL, 9mmole). The reaction mixture was heated at 60°-70° C. for 5hr with stirring. After cooling to room temperature, excess acetyl bromide was removed by concentration. Distillation of the reaction mixture under reduced pressure provided 276mg of the desired product as a colorless oil (45%, 100°-120° C./0.7 torr).

$^1$H NMR(CDCl$_3$, δ) 8.10-7.10(6H,m), 1.28(9H,s)

EXAMPLE 9

Methyl 1-bromo-1-(trimethylacetoxy)acetate

To methyl glyoxylate (2.0g, 23mmole) was added pivaloyl bromide (0.5mL, 57mmole). The reaction mixture was heated at 70° C. for 90min with stirring. After cooling to room temperature, excess propionyl bromide was removed by concentration. Distillation of the reaction mixture under reduced pressure provided 3.2g (62%, 70°-80° C./1 torr) of the desired product as a colorless oil.

$^1$H NMR(CDCl$_3$, δ) 6.85(1H,s), 3.91(3H,s), 2.45(2H,q,J=7Hz), 1.14(3H,t,J=7Hz)

We claim:

1. Ester derivatives of the following formula

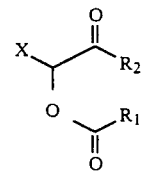

wherein, R$_1$ is methyl, ethyl, isopropyl, or t-butyl, R$_2$ represents methoxy, ethoxy, or isopropanoxy, and X represents Br.

2. A process for preparing ester derivatives as claimed in claim 1 which comprises reacting an aldehyde of general formula (III) and an acid halide of general formula (IV) at 20°-80° C. with or without solvents,

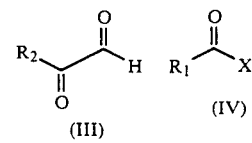

wherein R$_1$ is methyl, ethyl, isopropyl, or t-butyl, R$_2$ represents methoxy, ethoxy, or isopropanoxy, and X represents Br.

3. A process for preparing ester derivatives according to claim 2, wherein the solvent is selected from the group consisting of dichloromethane, chloroform, carbon tetrachloride, tetrahydrofuran, diethyl ether, ethyl acetate, n-hexane, n-pentane, or mixtures thereof.

4. A compound of claim 1, methyl bromoacetoxyacetate.

5. A compound of claim 1 ethyl bromoacetoxyacetate.

6. A compound of claim 1, isopropyl bromoacetoxyacetate.

7. A compound of claim 1, isopropyl 1-bromo-1-(trimethyl acetoxy) acetate.

8. A compound of claim 1, ethyl 1-bromo-1-trichloroacetoxy acetate.

9. A compound of claim 1, isopropyl 1-bromo-1-(cyclohexanecarboxy) acetate.

10. A compound of claim 1, methyl 1-bromo-1-(trimethylacetoxy) acetate.

* * * * *